United States Patent [19]
McDow

[11] Patent Number: 5,200,170
[45] Date of Patent: Apr. 6, 1993

[54] MEDICAL PROCESS—USE OF DICHLORODIFLUOROMETHANE ($CCL_2F_2$) AND CHLORODIFLUOROMETHANE ($CHCLF_2$) AS CRYOGENS FOR TREATING SKIN LESIONS

[76] Inventor: Ronald A. McDow, 1717 Nottingham Pl., Nashville, Tenn. 37221

[21] Appl. No.: 381,296

[22] Filed: Jul. 18, 1989

[51] Int. Cl.[5] .................. A61M 35/00; A01N 25/02; A61K 9/08; A61L 9/04
[52] U.S. Cl. ....................... 424/45; 424/43; 128/399; 128/400; 128/402; 128/403; 128/DIG. 27; 604/49; 604/289; 604/290; 604/291
[58] Field of Search ............. 424/47, 43, 45; 128/DIG. 27, 399, 400, 402, 403; 604/49, 291, 289, 290

[56] References Cited

U.S. PATENT DOCUMENTS

| | | | |
|---|---|---|---|
| 947,382 | 2/1909 | Goosmann | 128/399 |
| 2,536,001 | 6/1950 | Chase | 128/399 |
| 2,746,264 | 7/1956 | Keyes | 128/399 |
| 3,827,436 | 8/1974 | Stumpf et al. | 128/303.1 |
| 3,889,681 | 6/1975 | Waller et al. | 606/22 |
| 3,901,241 | 8/1975 | Allen, Jr. | 606/25 |
| 4,043,341 | 8/1977 | Tromovitch | 606/22 |
| 4,758,217 | 7/1988 | Gueret | 128/399 |
| 4,802,475 | 2/1989 | Weshahy | 128/27 |
| 4,865,028 | 9/1989 | Swart | 128/303.1 |
| 4,869,897 | 9/1989 | Chatterjge et al. | 424/47 |

FOREIGN PATENT DOCUMENTS 2172060 9/1973 France .

Primary Examiner—Thurman K. Page
Assistant Examiner—Carlos Azpuru
Attorney, Agent, or Firm—Parmelee, Bollinger & Bramblett

[57] ABSTRACT

Use of $CCl_2F_2$ or $CHClF_2$ to perform cryogenic surgery on a variety of skin lesions is described.

4 Claims, 1 Drawing Sheet

MEDICAL PROCESS—USE OF DICHLORODIFLUOROMETHANE (CCL₂F2) AND CHLORODIFLUOROMETHANE (CHCLF₂) AS CRYOGENS FOR TREATING SKIN LESIONS

BACKGROUND OF THE INVENTION

This medical treatment process will allow many more physicians and patients to receive cryosurgery at much less cost, less time involved in the procedure, and less complications such as infections and hypertrophic scarring than seen with conventional surgical and cryogenic methods. I estimate the cost of my medical process to be 1/100th of the cost of using liquid nitrogen since there is no evaporation of product, no need for expensive storage dewars, and no need for expensive delivery devices. Approximately 1/15th of the time is required for this process as compared to traditional scalpel surgery or electrodessication and curettage which most physicians currently use to treat these skin lesions. It is not possible to quantify the value of the physician's and patient's time saved. It is equally impossible to quantify in dollars the potential decrease in human suffering and permanent disfigurement avoided by using this process.

In conclusion the use of dichlorodifluoromethane and chlorodifluoromethane as cryogenic agents in clinical medicine has significant economical and cosmetic benefits for physicians and patients. I feel that disclosure of this material will be one of the most practical medical advances made this year.

FIELD OF THE INVENTION

The field of this invention relates to cryogenic surgery for skin lesions and mucous membranes, also vaginal and cervical lesions.

PRIOR ART

I have done a literature search of the medical literature and found no evidence of this in any publication and I am not aware of any clinical use of this cryogenic agent worldwide. Currently methods used are scalpel (cold steel) surgery, electrodessication, and use of liquid nitrogen.

The problems associated with liquid nitrogen as a cryogenic agent:
1. there is a 3-5% evaporation of product even if not used.
2. expensive storage dewars are required for liquid nitrogen ($600-$2500)
3. expensive delivery devices are required to spray this cryogen onto skin and mucous membranes ($700-$3000).

The problems associated with scalpel (cold steel) surgery:
1. bacterial skin infection rate up to 18% depending on sterile technique of the operator and heat and humidity of the location of surgery
2. hypertrophic scarring occurs up to 25% depending on the operator skill and patient genetic predisposition to scar
3. inefficient use of time; most minor scalpel surgery procedures require 25 to 50 minutes time to perform. This time is required for
   a) anesthetizing the treatment area,
   b) 5 minutes waiting period before lidocaine is optimally effective,
   c) preparing a sterile operating field,
   d) performing the surgical procedure.

The problems associated with electrodessication:
1. time consuming due to need for local anesthetic
2. causes permanent hypertrophic scarring in a significant percentage of patients.

Example of the literature discussing some of these prior art methods and corresponding problems is *Skin Surgery* by Ervin Epstein and Ervin Epstein, Jr. 6th edition, Philadelphia, W. B. Saunders, 1987, pages 180–182 which includes pictures of facial hypertrophic scarring following curettage and electrodesiccation.

BRIEF DESCRIPTION OF INVENTION

My medical process solves these problems:
1. it is portable (it can be carried from office to office or office to hospital)
2. it is more time-efficient for patient and physician
3. it is less expensive for the physician and therefore can be more widely afforded and used by more physicians
4. its use has fewer side effects than scalpel surgery (lower infection rates and scarring).

This process and cryogenic agent has been reviewed and approved by the FDA (from evidence that I have submitted to the FDA in confidence). The FDA approval number is K881349. Broadly, my invention is to bring skin temperature to $-30°$ C. to $-80°$ C. in order to cause destruction of targeted lesions.

DETAILED DESCRIPTION OF THE INVENTION OF THE MEDICAL PROCESS

Dichlorodifluoromethane ($CCl_2F_2$) is sprayed from 12 to 16 ounce aerosol cans through a one millimeter capillary applicator tube measuring 13 cm in length. This applicator tube is held 5 cm from the lesion being treated. This distance may vary approximately 2 cm to 3 cm each way. Through this procedure the spray is concentrated more precisely to the area being treated. The spray is focused into an appropriate sized constricting device which surrounds the lesion being treated. These constricting devices may be neoprene cones or commonly available otoscopic cones. A ten to twenty second direct freeze application is used on most benign lesions. The duration of spray can be varied according to the size and thickness of the lesion. The dichlorodifluoromethane does not evaporate immediately after contacting the skin but rather accumulates within the cones or constricting devices and continues to freeze ten to twenty seconds after the spraying ceases. After evaporation is complete lesions being treated turn white. This represents the beginning of the thaw stage which averages 45–65 seconds. Extreme care must be taken not to touch the lesions during this thaw stage. The heat from a finger or other body part would decrease the thaw time and diminish the cellular destructive potential of the cryogen. A second and third freeze-thaw cycle may be performed depending on the thickness and width of the lesion being treated. Lidocaine may be used as a local anesthetic prior to freezing in extremely sensitive patients but it is usually not necessary. Post-operative care includes leaving the lesion exposed to air unless a drainage develops, cleaning the lesion with peroxide daily, and allowing the ensuing crust formation to spontaneously detach.

A similar technique can be used with chlorodifluoromethane ($CHClF_2$).

Figure 1:
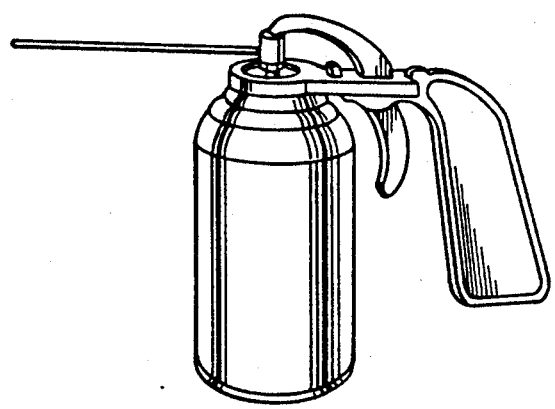
FIG. 1 is a perspective view of a refrigerant dispensing device usable with the present invention.
Figure 2:
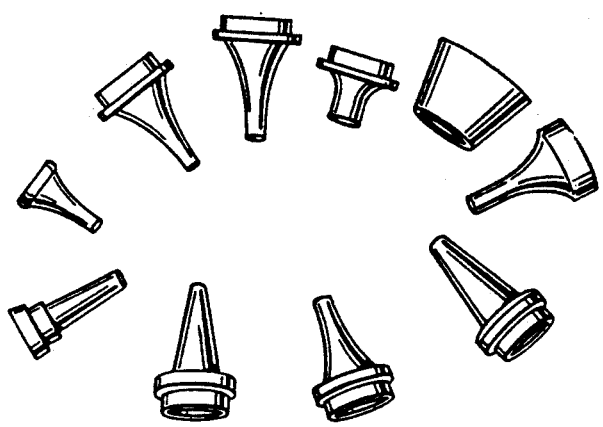
FIG. 2 illustrates a plurality of fluid retaining devices usable in the invention.

To illustrate my invention in more detail and the best ways for carrying out its operation, FIG. 1 discloses the cryogenic agent packaged in a 12 ounce can and dispensed through an aerosol nozzle. A 1 mm capillary tube is attached to direct the spray accurately into constricting devices which are illustrated in FIG. 2. A snap-on handle with trigger device is also shown. This allows an appropriate amount of freezing agent to be dispensed while protecting the physician's hands and fingers from freezing.

FIG. 2 reveals a variety of inexpensive constricting devices which are to be used to limit the spread of freeze. An approximate size diameter tip should be chosen to match the size of the lesion being frozen.

Figure 3:
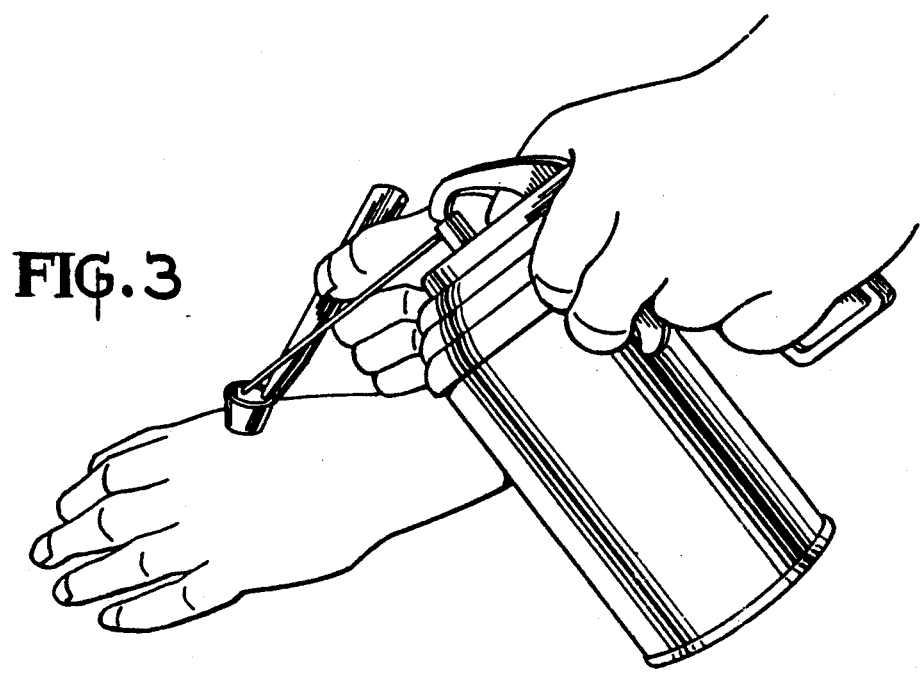
FIG. 3 illustrates the application of a refrigerant from the dispensing device onto a lesion by use of a fluid retaining device.

FIG. 3 demonstrates the use of the device. The agent is sprayed into the cone as described in the first paragraph of this "detailed description" of the technique.

EXAMPLES

Evidence of the effectiveness of this invention was established by treating a total of 75 verruca lesions. Verruca lesions in the study included 33 verruca digitata and periungual lesions, 11 verruca plana lesions, and 31 verruca vulgaris lesions.

Expected erythema occurred. It was noted that the erythema occurred between one and two hours after freezing. Bulla formation was seen in the patients within one to two days. Sloughing of the lesions occurred between 5 and 12 days. Complete healing usually resulted within 18 days. Of the 75 verruca treated, 67 showed complete destruction and no recurrence at six months. Six showed incomplete sloughing after one freezing but cleared after a second treatment with no recurrence at six months. Two lesions showed recurrence within six months but cleared after treatment.

No complications occurred, and rapid healing progressed with some slight temporary hypopigmentation in some patients. The minimal discomfort experienced by patients during treatment varied among patients according to the pain threshold of each.

The Food and Drug Administration (FDA) has reviewed this data in case number K881349 and has approved dichlorodifluoromethane and chlorodifluoromethane to be marketed to physicians for clinical use under the name Verruca-Freeze ™ Cryotherapy Delivery System for lesions now being treated by liquid nitrogen.

The skin lesions which can be treated by the cryosurgery method carried out in accordance with this invention may collectively be referred to as benign epithelial skin lesions in addition to basal and squamous cell carcinoma which include acne, actinic keratosis, skin tags, adenoma sebaceum, angioma, carbuncle, chondrodermatitis nodularis helicis, chromblastomycosis, cutaneous horn, granuloma annulare, granuloma pyogenicum, hidradenitis suppurativa, histiocytoma, herpes simplex, herpes zoster, keloid, keratocanthoma, lentigenes, lupus vulgaris, molluscum contagiosum, mucous cysts, nevi, porokeratosis, seborrheic keratosis, sebaceous hyperplasia, steatocystoma multiplex, rhinophyma, tattos, and verruca (warts).

The invention which is claimed is:

1. A method of cryogenically treating a skin lesion comprising the steps of:
    (a) placing a hollow fluid retaining device having a side wall defining a bottom open end of a size slightly greater than a skin lesion to be removed by cryosurgery and a top open end in an upright position in which said bottom open end seals against a patient's skin entirely surrounding said skin lesion and said top open end is above said bottom open end,
    (b) introducing into said top open end of said upright fluid retaining device from a container separate from said fluid retaining device a liquid cryogenic agent selected from the group consisting of chlorodifluoromethane and dichlorodifluoromethane to cause a liquid pool of said cryogenic agent to contact directly the entire area of said skin lesion for a period of time to permit said cryogenic agent to reduce the temperature of said skin lesion to a temperature no higher than $-30°$ C.,
    (c) terminating said introducing step,
    (d) retaining said hollow fluid retaining device in said upright position surrounding said skin lesion after said introducing step has been terminated in order to accumulate and retain said liquid cryogenic agent within said bottom open end of said fluid retaining device and in contact with said skin lesion in order to maintain said skin lesion at said reduced temperature while said cryogenic agent is evaporating, and
    (e) subsequently removing said fluid retaining device from said upright position after said liquid cryogenic agent has evaporated.

2. The method according to claim 1 further comprising the step of permitting said skin lesion to completely thaw after said step of removing said fluid retaining device, and sequentially repeating said steps of placing said hollow fluid retaining device in said upright position, introducing said cryogenic agent into said top open end of said fluid retaining device, terminating said introducing step and retaining said hollow fluid retaining device in said upright position while said cryogenic agent is evaporating, and subsequently removing said fluid retaining device from said upright position.

3. The method according to claim 1 in which said period of time for said introducing step is approximately 10–20 seconds when said skin lesion is benign.

4. The method according to claim 1 in which said step of retaining said hollow fluid retaining device in said upright position continues for a time period of approximately 10–20 seconds.

* * * * *